(12) United States Patent
Simon (10) Patent No.: US 9,687,391 B2
(45) Date of Patent: Jun. 27, 2017

(54) FLEXIBLE ABSORBENT AND SEALING SYSTEMS FOR SURGICAL DEVICES

(71) Applicant: Victoria Genevieve Simon, Little Egg Harbor, NJ (US)

(72) Inventor: Victoria Genevieve Simon, Little Egg Harbor, NJ (US)

(*) Notice: Subject to any disclaimer, the term of this patent is extended or adjusted under 35 U.S.C. 154(b) by 599 days.

(21) Appl. No.: 14/197,291

(22) Filed: Mar. 5, 2014

(65) Prior Publication Data

US 2014/0276514 A1  Sep. 18, 2014

Related U.S. Application Data

(60) Provisional application No. 61/800,645, filed on Mar. 15, 2013.

(51) Int. Cl.
A61F 13/36 (2006.01)
A61B 90/70 (2016.01)

(52) U.S. Cl.
CPC .............. *A61F 13/36* (2013.01); *A61B 90/70* (2016.02); *A61B 2090/701* (2016.02)

(58) Field of Classification Search
CPC ..... A61B 90/70; A61B 2090/701; B08B 9/00; B08B 9/02; B08B 9/027; B08B 9/04
See application file for complete search history.

(56) References Cited

U.S. PATENT DOCUMENTS

| | | | |
|---|---|---|---|
| 882,598 A * | 3/1908 | Ward | F41A 29/02 15/104.066 |
| 3,736,935 A | 6/1973 | Reimels | |
| 5,203,767 A * | 4/1993 | Cloyd | A61F 13/36 604/11 |
| 5,407,423 A | 4/1995 | Yoon | |
| 5,972,125 A * | 10/1999 | Hedge | F41A 29/02 134/8 |
| 6,045,623 A | 4/2000 | Cannon | |
| 6,699,331 B1 | 3/2004 | Kritzler | |
| 7,695,468 B2 * | 4/2010 | Dario | A61B 17/221 606/11 |
| 8,185,997 B2 | 5/2012 | Heck | |
| 8,479,344 B2 * | 7/2013 | Maslanka | A61B 1/122 15/104.05 |
| 8,490,235 B2 | 7/2013 | Soetermans | |
| 8,566,995 B2 | 10/2013 | Asano et al. | |
| 9,228,790 B2 * | 1/2016 | Stephens | F41A 29/02 |
| 9,339,349 B2 * | 5/2016 | Pisacane | B08B 9/027 |
| 2010/0139018 A1 | 6/2010 | Maslanka | |

* cited by examiner

*Primary Examiner* — Randall Chin
(74) *Attorney, Agent, or Firm* — Doherty IP Law Group LLC (57) ABSTRACT

A system for absorbing blood and bodily fluids during surgical procedures includes an elongated, flexible element having a proximal end and a distal end, a weight secured to the distal end of the elongated, flexible element, and a plurality of absorbent elements attached to the elongated, flexible element. The absorbent elements are spaced from or connected to one another along the length of the elongated, flexible element. The absorbent elements, such as sponges or cotton balls, are adapted for soaking up blood and bodily fluids at a surgical site. A tab is secured to the proximal end of the elongated, flexible element for extracting the absorbent elements from the surgical site.

18 Claims, 9 Drawing Sheets

FLEXIBLE ABSORBENT AND SEALING SYSTEMS FOR SURGICAL DEVICES

CROSS-REFERENCE TO RELATED APPLICATIONS

The present application claims benefit of U.S. Provisional Application Ser. No. 61/800,645 filed Mar. 15, 2013, the disclosure of which is hereby incorporated by reference herein.

BACKGROUND OF THE INVENTION

Field of the Invention

The present application is generally directed to surgical instruments and surgical procedures, and is more particularly related to systems, devices and methods for controlling and collecting blood and bodily fluids at surgical sites and cleaning surgical instruments in situ at a surgical site.

Description of the Related Art

During surgery, and particularly during laproscopic and endoscopic surgeries, large quantities blood and bodily fluids accumulate at the surgical site. The blood and bodily fluids must be collected and removed from the surgical site so that it remains clear of blood and bodily fluids, and to maintain good visibility for the surgeon.

A number of devices and methods have been developed for removing fluids from a surgical site. A first method involves using a vacuum to suction blood and bodily fluids from a surgical site, however, using a vacuum during laproscopic or endoscopic surgeries can result in deflation of the cavity. As a result, using a vacuum during these types of procedures is not viewed as a safe and effective choice by many surgeons.

Another procedure involves using gauze to swab and/or blot up the blood and bodily fluids present at a surgical site. Although gauze is relatively easy to use during open surgical procedures, it is much more difficult to use during laproscopic surgeries. A typical drawback involves the gauze bunching up or sticking inside the trocar as it is pushed toward the surgical site. Another drawback involves attempting to push a sufficient quantity of gauze through the trocar port, which is somewhat similar to pushing a rope down an enclosed tube. Typically, the gauze gets jammed in the trocar and cannot be pushed, in which case the trocar may need to be removed, which could traumatize the patient. Yet another drawback to using separate gauze sheets or balls is that the gauze inserted into the patient may become lost or be left behind at the end of the surgery. Leaving gauze inside a patient can cause myriad problems including infection, post-surgery complications, and an increased potential for costly malpractice claims. Yet another complication associated with using gauze is that the volume of fluid that may be absorbed is limited.

Moreover, since gauze expands or swells as it soaks up fluids, when the gauze is removed through the trocar, it is compressed, whereby the fluid in the blood soaked gauze drips back into the body through the trocar, allowing collected fluids back into the surgical field. These fluids that drip back into the surgical site could contain dead tissue, old blood, removed tissue particles, and saline mixed with blood, all of which must be removed from the patient to limit post surgical adhesions and minimize the possibility of infection.

In addition, when removing bloody gauze from a surgical site, the trocar or other instruments may become bloody and/or contains tissue particles that can soil the instruments and optical lenses, requiring more time during the surgery to clean the trocar and the associated instrument.

In view of the above, there remains a need for systems, devices and methods for reliably and efficiently removing blood and bodily fluids from surgical sites during surgical procedures. There also remains a need for systems, devices and methods that are capable of cleaning surgical instruments, such as a trocar, of blood and tissue during surgical procedures.

SUMMARY OF THE INVENTION

In one embodiment, a system for absorbing blood and bodily fluids during surgical procedures preferably includes an elongated, flexible element having a proximal end and a distal end, a weight secured to the distal end of the elongated, flexible element, and one or more absorbent elements, such as sponges or cotton balls, attached to the elongated, flexible element, whereby the one or more absorbent elements are adapted for soaking up blood and bodily fluids at a surgical site.

In one embodiment, the one or more absorbent elements include a plurality of absorbent elements attached to the elongated, flexible element, whereby the absorbent elements are spaced from one another along the length of the elongated, flexible element.

In one embodiment, an anchor tab, such as a pull ring, is secured to the proximal end of the elongated, flexible element. In one embodiment, the anchor tab or pull ring is sized so that it is larger than the inner diameter of the trocar so that the tab or ring may not fall into the trocar and become lost inside a patient's body. The larger relative size of the tab or ring desirably insures that the tab or ring will remain outside the body and cannot fit into the trocar. When it is desirably to remove the absorbent elements from the trocar, the tab or ring is pulled for retrieving the absorbent elements. In one embodiment, the absorbent elements are attached to the elongated, flexible element at positions that are closer to the weight (i.e., the distal end) than the anchoring tab (i.e., the proximal end). The anchor tab may have a code provided thereon for auditing and accountability purposes.

In one embodiment, a sealing element covers a distal end of one or more of the absorbent elements, such as a distal-most one of the plurality of absorbent elements. In one embodiment, a sealing element may have a grip element located at a distal end of the sealing element that is adapted to be held by a surgical tool for being moved about a surgical site for absorbing blood and bodily fluids. In one embodiment, the sealing element has a proximal end having a cup shape that covers the distal end of the distal-most absorbent element, and the grip element protrudes from the distal end of the cup shaped proximal end. In one embodiment, a sealing element covers a distal end of each of the absorbent elements. The sealing elements are preferably more rigid than the absorbent elements.

In one preferred embodiment, a cup shaped proximal end of a sealing element has an elongated reservoir that is located distal to an absorbent element thus creating a space for the collection of fluids between the distal end of the absorbent element and the proximal face of the elongated reservoir of the cup shaped sealing element. In one embodiment, the reservoir volume may be adjusted in response to the degree of fluid management that is required. In one embodiment, a sealing element preferably includes a relatively thin, flexible protruding membrane located near the proximal rim of the sealing element. The protruding membrane may be perpendicular or may be angled in the proximal direction so as to further cup and collect dripping fluids as the absorbent elements are being removed from a trocar. The thin, flexible protruding membrane may also serve to effectively communicate with a range of potentially larger trocar ports for enabling the removal of swollen absorbent components with reduced fluid loses.

In one embodiment, a system includes a surgical tool, such as a trocar, having an elongated, tubular opening (e.g., a trocar opening) with an inner diameter. In one embodiment, a sealing element preferably has an outer diameter that communicated with the inner diameter of the elongated, tubular opening.

In one embodiment, a method of using the system disclosed herein desirably includes inserting the trocar into a surgical opening and advancing a distal end of the trocar to a surgical site, introducing the weight secured to the distal end of the elongated, flexible element into the trocar opening, and lowering the weight and the absorbent elements attached to the elongated, flexible element through the trocar opening until the weight and the absorbent elements are advanced beyond the distal end of the trocar and are disposed adjacent the surgical site. In one embodiment, the absorbent elements are advanced through a trocar and positioned at a surgical site as seen fit by a surgeon.

In one embodiment, the method may include using a surgical instrument for engaging the weight secured to the distal end of the elongated, flexible element for pulling the elongated, flexible element and the absorbent elements through the trocar opening and from the distal end of the trocar, using the surgical instrument for engaging the gripping element located at the distal end of the sealing element for manipulating the absorbent element at the surgical site for absorbing blood and bodily fluids at the surgical site, and using the tab secured to the proximal end of the elongated, flexible element for pulling the elongated, flexible element, the absorbent elements and the weight toward the proximal end of the trocar opening for removing the absorbent elements from the surgical site.

In one embodiment, a system for absorbing blood and bodily fluids during surgical procedures desirably includes an elongated, flexible element, such as a flexible core, having a proximal end and a distal end, a weight secured to the distal end of the elongated, flexible element, a plurality of absorbent elements (e.g., sponges or cotton balls) attached to the elongated, flexible element, whereby the absorbent elements are spaced from one another along the length of the elongated, flexible element, and whereby the absorbent elements are adapted for soaking up blood and bodily fluids at a surgical site, and a tab secured to the proximal end of the elongated, flexible element.

In one embodiment, sealing elements cover the distal ends of each of the absorbent elements. The sealing elements may be more rigid than the absorbent elements. In one embodiment, the absorbent elements are preferably closer to the distal end of the elongated, flexible element than the proximal end of the elongated, flexible element so that the proximal end of the elongated, flexible element remains outside of the trocar when the absorbent elements are positioned at the surgical site, thereby insuring that none of the absorbent elements are left behind at the surgical site at the end of a surgical procedure.

In one embodiment, a flexible absorbent sealing system preferably includes a flexible, elongated cord having a proximal end with a pull ring or grip and a distal end with a weight. The flexible absorbent system preferably has one or more absorbent elements (e.g., sponges, cotton balls) that are attached to the flexible cord and spaced from one another along the length of the flexible cord. The absorbent elements are designed to soak up blood and bodily fluids inside a patient at a surgical site. The absorbent elements may have various shapes (e.g., spherical, bullet, square, rectangular), various sizes (e.g., small, medium and large), and various absorbent properties and/or qualities. In one embodiment, at least one of the absorbent elements has a distal end seal having an outer diameter that substantially matches or communicates with the inner diameter of a cannulated surgical instrument, such as a trocar. As the absorbent element passes through the trocar, the distal end seal preferably retains fluid as it wipes the inner diameter of the instrument for cleaning the instrument of blood, tissue, and/or debris so as to provide good visibility for the surgeon. In one embodiment, the distal end seal may have an elongated reservoir that provides a space between the distal end of the absorbent element and the proximal face of the cup shaped portion of the sealing element. In one embodiment, a proximal rim of a cup shaped portion of the distal end seal may include a thin, flexible membrane that extends outwardly or proximally toward the proximal end of the flexible, elongated cord.

In one embodiment, the flexible absorbent sealing system may have one or more absorbent-sealing elements along the length of the cord to increase absorbency without increasing the difficulty of removing a large absorbent element and incurring dripping back into the body cavity. The flexible absorbent sealing system preferably minimizes repetitive motions of constant sponge replacement into a single combined motion. The system disclosed herein also desirably reduces the risk of leaving a sponge, gauze, or absorbing element, because all of the absorbent elements are attached to the flexible cord, which has a proximal end with that remains outside the body at all times.

In one embodiment, the present invention provides a system for preventing collected blood and fluids from re-entering the body upon gauze removal during endoscopy surgery.

In one embodiment, the flexible absorbent sealing system disclosed herein enables surgical personnel to use a single device to both remove one or more used absorbent elements through a trocar and simultaneously clean the trocar during removal of the used absorbent elements.

The present invention also prevents a new, clean gauze or absorbent element from getting dirty upon entry into a dirty trocar.

The present invention also preferably eliminates the need for a separate cleaning operation to clean a trocar after a used, bloody absorbent element has been removed from the trocar.

The system disclosed herein enables surgical personnel to maximize the volume of blood and fluid retrieved by using numerous smaller connected absorbent elements that each fit into a properly sized trocar, while limiting the release of the absorbed blood and fluid.

In one embodiment, the flexibility of the cord enables the individual absorbent elements to be positioned where needed inside the body. The flexibility of the cord enables two or more absorbent elements to be packed together to absorb blood and fluids, or to function as a dam to halt the flow of blood and fluids.

In one embodiment, a system may have absorbent elements having different sizes to accommodate different sized trocars and instruments.

In one embodiment, the system may include radio opaque material that is detectable with radiology. In one embodiment, at least one of the absorbent elements includes a radio opaque material.

In one embodiment, the distal end of the flexible cord has a weight that may be lowered into the trocar and grasped by a clamping element for pulling the absorbent elements through the trocar and into a body cavity. As such, the absorbent elements on the flexible cord may be selectively pushed or pulled through the trocar in either direction.

In one embodiment, larger sized absorbent elements may be used when increased absorbency is required.

In one embodiment, flexible cords having different lengths may be utilized to provide for systems that are short, medium and long.

In one embodiment, at least one of the absorbent elements has a spherical shape adjacent to a trocar seal.

In one embodiment, at least one of the absorbent elements has at least one flat shape adjacent to a trocar seal In one embodiment, at least one of the absorbent elements has at least one cylindrical shape, at least one bullet shape, or at least one egg shape adjacent to a trocar seal.

The flexible cord interconnecting the absorbent elements may include a colored or non-colored connection line attached to the absorbent elements and the trocar seal.

The system may be made of various bio-compatible surgical materials including but not limited to plastics, polymers, silicones, polyurethanes, composite polymers/monomers, stainless steels, of braided or monofilament structures as well as all known absorbent material including super absorbent materials, materials that react in the presence of blood or other fluids and other such materials known by those skilled in the art.

In one embodiment, a proximal end of the flexible cord has an anchor tab for being secured outside the body. The anchor tab may be coded for auditing and accountability purposes.

The distal end of the flexible cord may be weighted so that it falls freely down through the trocar, and so that the distal end of the cord may be easily seen and grasped. In one embodiment, a system may include a compressed absorbent both pre and post contact with fluids which may drop freely down a trocar prior to being exposed to fluids. As such, the device does not need to be pulled or pushed as described for other embodiments disclosed herein.

The distal seal may be made from any material that will prevent fluid dripping back into the trocar during removal of used absorbent elements. In one embodiment, the distal seal may have a grip member that can be used to grasp and position an absorbent element during surgery or to clean/wipe a specific surgical site or instrument during surgery. The distal seal may be made of materials including but not limited to silicone, rubber, polymers, non-absorbent cloth, etc. The seals may or may not have selective movability along the length of the flexible cord.

The flexible absorbent sealing system disclosed herein is preferably safer, more user friendly for both surgeons and patients, and more efficient at fluid management than can be obtained when using conventional un-tethered gauze or sponges in a closed surgical procedure.

The flexible absorbent sealing system disclosed herein has less fluid loss/drip upon removal through a trocar as compared to the same weight gauze pad or cotton balls with retained fluids.

These and other preferred embodiments of the present invention will be described in more detail below.

DETAILED DESCRIPTION

Figure 1:
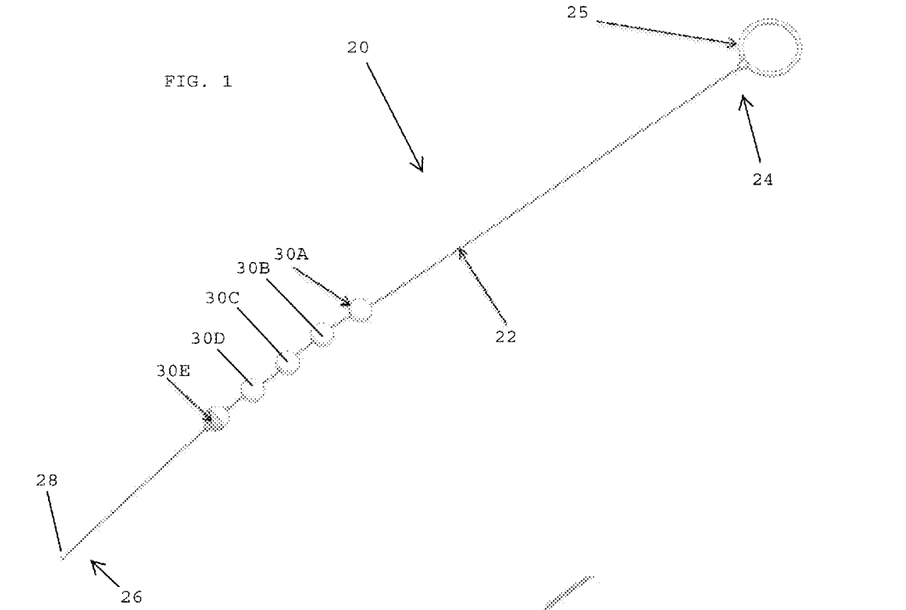
FIG. 1 shows a flexible absorbent and sealing system including a flexible cord and absorbent elements attached to the flexible cord, in accordance with one embodiment of the present invention.

Referring to FIG. 1, in one embodiment, a flexible absorbent and sealing system 20 preferably includes a flexible cord 22 having a proximal end 24 and a distal end 26. The system preferably includes a pull ring 25 attached to the proximal end 24 of the cord 22 and a weight 28 attached to the distal end 26 of the cord 22. The system 20 desirable includes a plurality of absorbent elements 30A-30D that are attached to the cord 22 and that are spaced from one another along the length of the cord 22. In FIG. 1, five absorbent elements 30A-30E are shown, however, other embodiments may have fewer or more spaced absorbent elements (e.g., 20) and still fall within the scope of the present invention.

Figure 2:
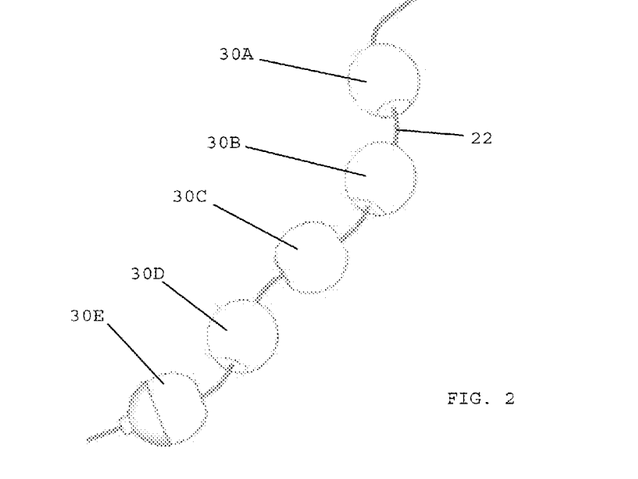
FIG. 2 shows a magnified view of the flexible cord and the absorbent elements shown in FIG. 1.

Referring to FIGS. 1 and 2, the absorbent elements 30A-30E are adapted to absorb and soak up blood, bodily fluid, tissue, and other debris that is present at a surgical site.

The absorbent elements are preferably made of materials that have the ability to soak up and absorb liquids such as cotton balls and sponges. The absorbent elements 30A-30E are attached to and evenly spaced from one another along the length of the flexible cord 22. The flexibility of the cord 22 enables the individual absorbent elements to be manipulated and moved relative to one another, yet remain attached to the flexible cord at all times. In one embodiment, the flexibility of the cord 22 enables two or more of the absorbent elements 30A-30D to be bunched together to absorb a large pool of blood/fluid, or to form a dam at a surgical site to stop the flow of blood/fluid.

Figure 3:
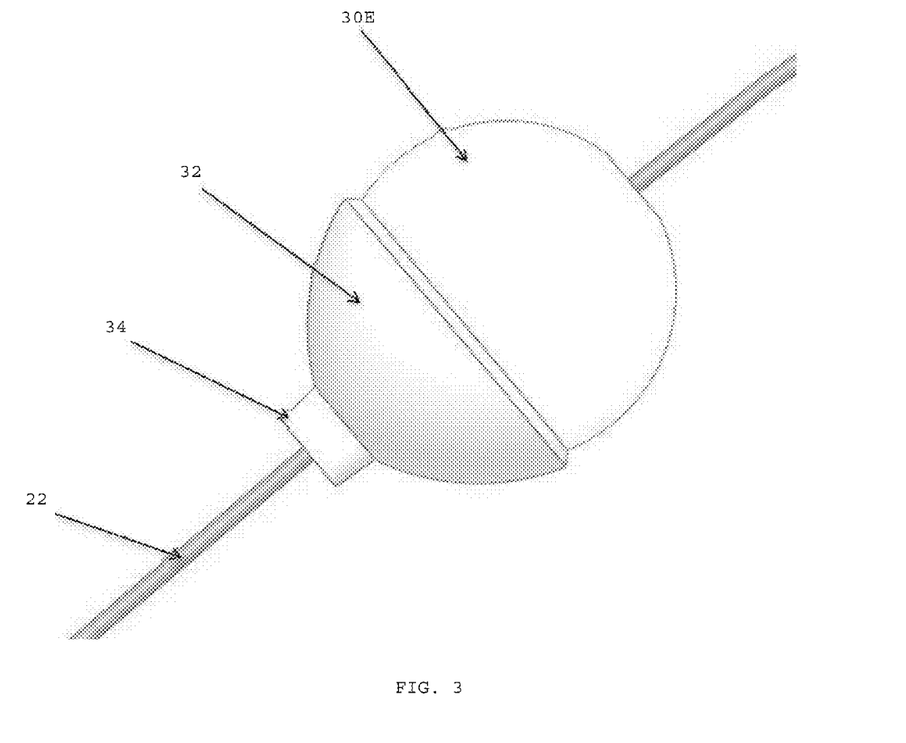
FIG. 3 shows a magnified view of a distal-most absorbent element shown in FIG. 2 including a distal end seal covering a distal end of the absorbent element, in accordance with one embodiment of the present invention.

Referring to FIGS. 2 and 3, in one embodiment, the distal-most absorbent element 30E on the flexible cord 22 has a seal/wipe element 32, which has an outer diameter that preferably matches or communicates with the inner diameter of a trocar used with the system 20. The size of the seal/wipe element 32 can be modified to match the inner diameter of a trocar. The seal/wipe element 32 is preferably used to wipe and/or seal the trocar as the distal-most absorbent element 30E is pulled proximally through the torcar. The distal end of the seal/wipe element 32 has a grip element 34 that enables the distal-most absorbent element 30E to be held between the jaws of a clamping tool. The grip element 34 enables the absorbent element 30E to be held and moved around a surgical site as necessary to collect blood, fluid, tissue, etc.

Figure 4A:
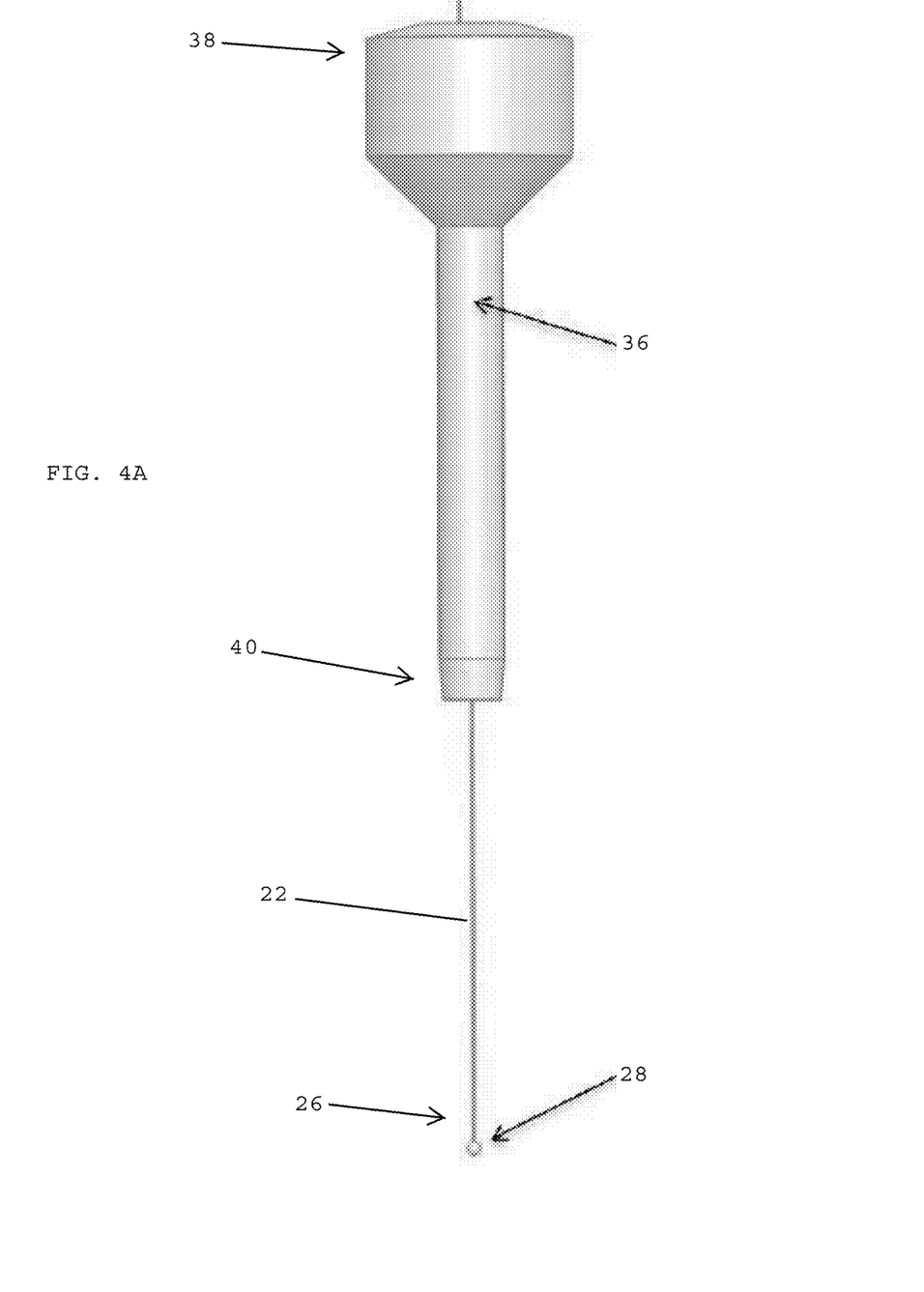
FIGS. 4A-4C show the flexible absorbent and sealing system of FIG. 1 being inserted into a trocar, in accordance with one embodiment of the present invention.
Figures 4B, 4C:
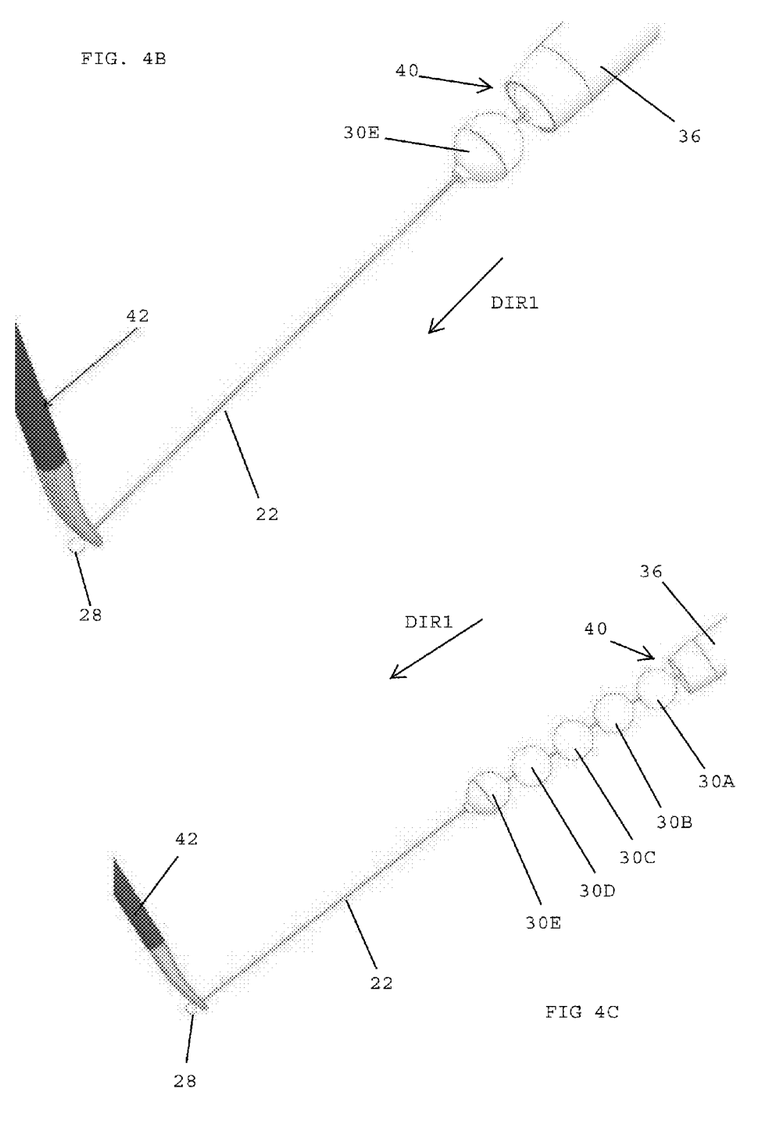

Referring to FIGS. 4A-4C, in order to deploy the absorbent elements 30A-30E at a surgical site inside a patient, the distal end 26 of the flexible cord 22 may be passed through a trocar 36 having a proximal end 38, a distal end 40, and a trocar opening that extends from the proximal end to the distal end. The weight 28 attached to the distal end of the flexible cord 22 preferably enables the cord to easily pass through the trocar opening. Once the weight falls below the distal end 40 of the trocar 36, a surgical tool 42, such as a surgical grip, may be utilized to grasp the weight for pulling the flexible cord 22 and all of the absorbent elements 30A-30E attached to the flexible cord beyond the distal end 40 of the trocar 36 in the direction Designated DIR1. Once the absorbent elements 30A-30E have been pulled beyond the distal end 40 of the trocar 36, the absorbent elements are preferably disposed inside a patient, adjacent a surgical site.

Figure 5:
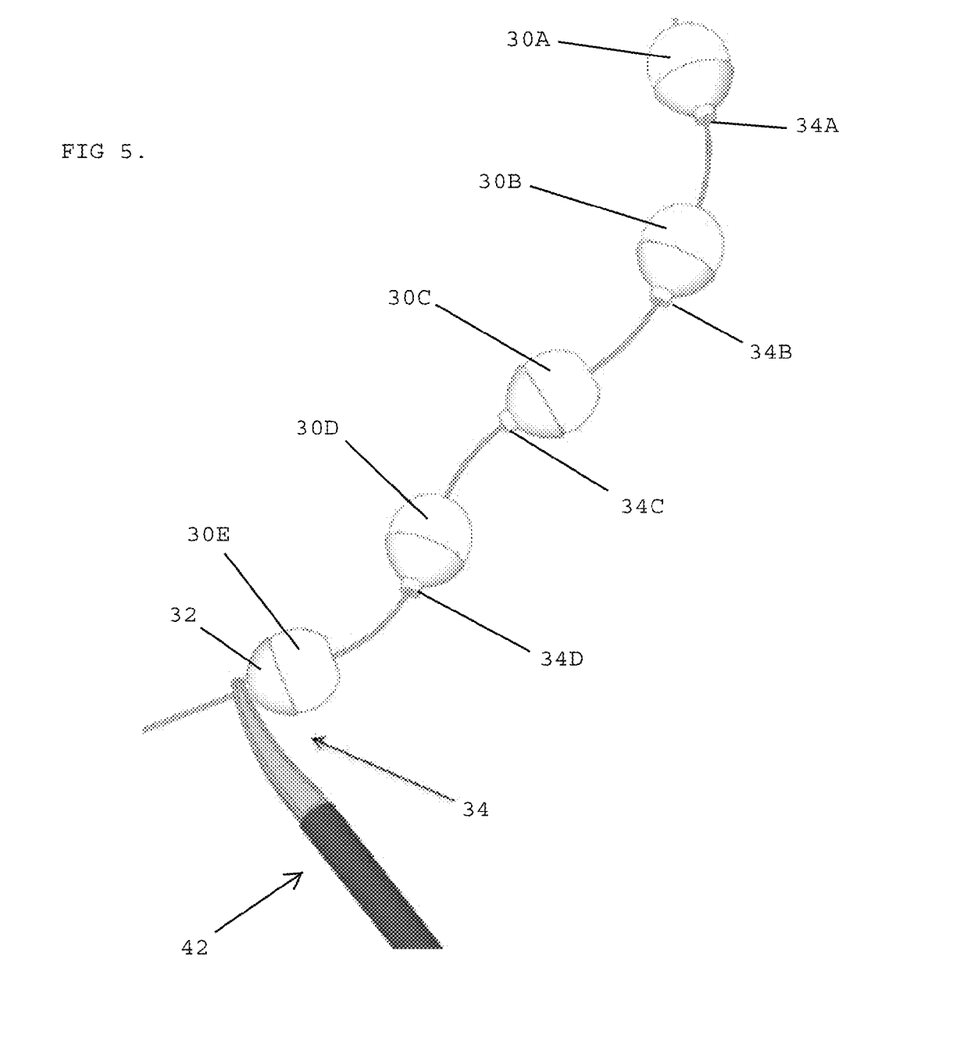
FIG. 5 shows the distal absorbent element of FIG. 2 being gripped by a clamping device.

Referring to FIG. 5, in one embodiment, the surgical tool 42 is used to grab the grip element 34 (FIG. 3) provided on the seal/wipe element 32. In one embodiment, the absorbent element 30E may be manipulated at the surgical site by holding the grip element 34 of the seal/wipe element 32. By utilizing the grip element 34 on the seal/wipe element 32, the absorbent portion of the absorbent element 30E will not be squeezed and will not lose its contents (e.g., previously absorbed blood). The other absorbent elements 30A-30D may also be moved to collect fluid by using the surgical grips 42 to grasp the respective grip elements 34A-34D.

Figure 6A:
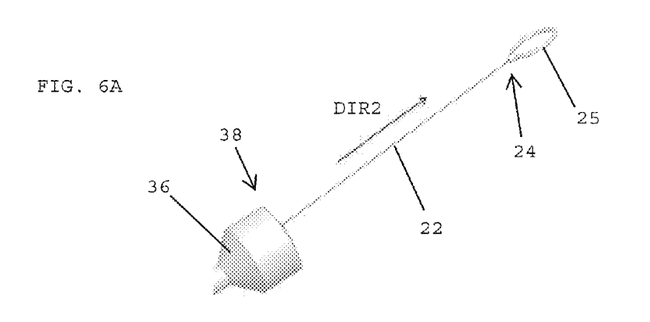
FIGS. 6A-6C show the flexible absorbent and sealing system of FIG. 1 being extracted from a trocar, in accordance with one embodiment of the present invention.
Figure 6B:
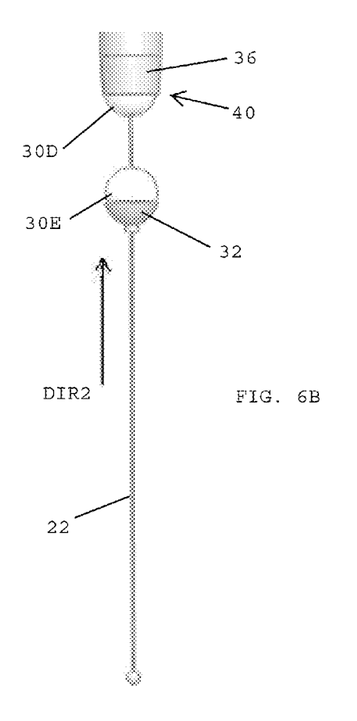
Figure 6C:
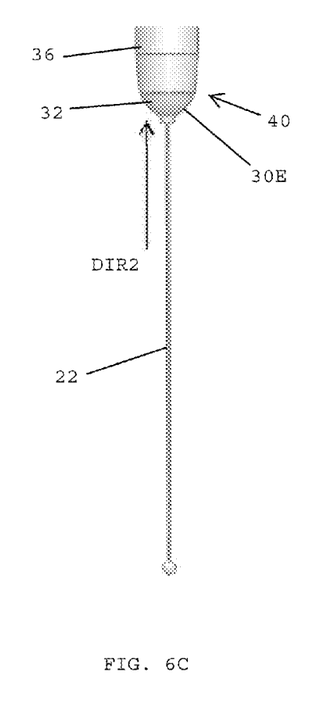

Referring to FIGS. 6A-6C, in one embodiment, after the absorbent elements 30A-30E have been utilized to collect blood, fluid, tissue and debris at the surgical site, the absorbent elements may be pulled proximally through the trocar 36 for removal from the patient. In one embodiment, the pull ring 25 at the proximal end 24 of the flexible cord is pulled away from the proximal end 38 of the trocar 36 in the direction DIR2. FIG. 6B shows the flexible cord being pulled in the direction DIR2 with the fourth absorbent element 30D entering the trocar opening at the distal end 40 of the trocar 36. As the fourth absorbent element 30D is pulled through the trocar, it may clean the inside of the conduit extending through the trocar. FIG. 6C shows the distal absorbent element 30E with the seal/wipe 32 upon reaching the opening at the distal end 40 of the trocar 36. The seal/wipe 32 preferably has an outer diameter that closely matches or communicates with the inner diameter of the trocar opening for wiping clean the inside of the trocar opening as the seal/wipe 32 passes from the distal end to the proximal end of the trocar 36. The tight seal between the seal/wipe element 32 and the trocar opening prevents fluid from dripping back inside the patient and wipes the trocar opening clean.

Figure 7:
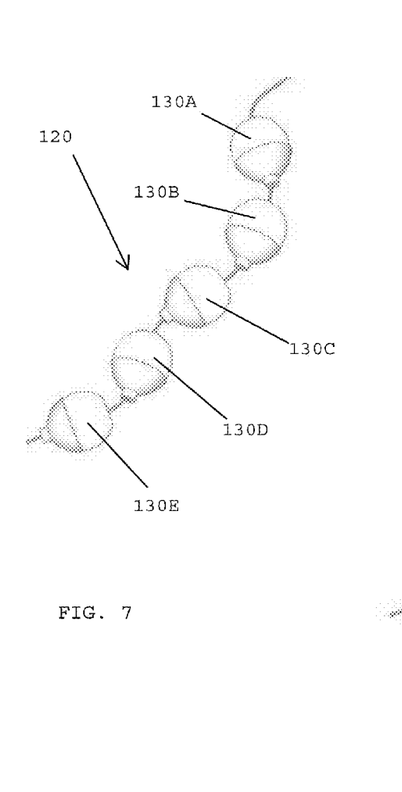
FIG. 7 shows a flexible absorbent and sealing system including a flexible cord and absorbent elements that are closely spaced from one another on the flexible cord, in accordance with one embodiment of the present invention.
Figure 8:
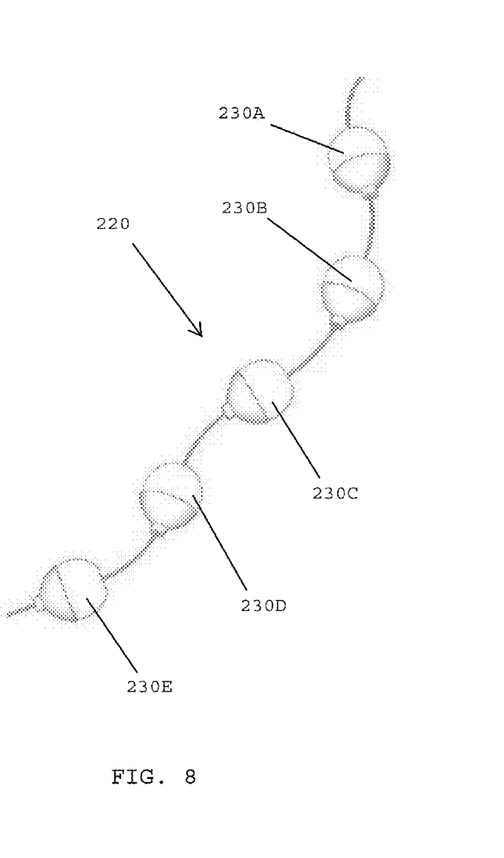
FIG. 8 shows a flexible absorbent and sealing system including a flexible cord and absorbent elements that are widely spaced from one another on the flexible cord, in accordance with one embodiment of the present invention.

Referring to FIGS. 7 and 8, in one embodiment, the spacing between the absorbent elements may vary. In FIG. 7, a flexible absorbent sealing system 120 includes a first set of absorbent elements 130A-130E that are spaced more closely together than a second set of absorbent elements 230A-230E of a second flexible absorbent sealing system 220, shown in the embodiment of FIG. 8. Alternately, the absorbent elements may each have a tubular core that allows them to move along the length of the flexible cord. There may, therefore, be no fixed spacing and the absorbent elements may move freely on the flexible cord having a space between or no space between each absorbent element. Although five absorbent elements are shown in each embodiment, the number of absorbent elements attached to a flexible cord may be as few as one or as many as twenty or more.

Figure 9:
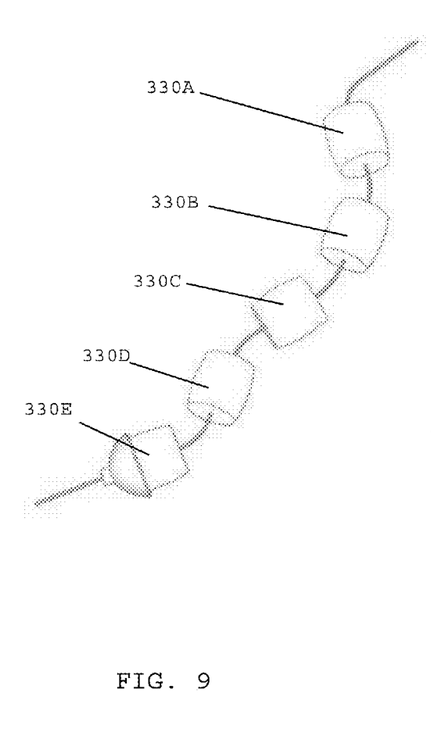
FIG. 9 shows a flexible absorbent and sealing system including a flexible cord and absorbent elements having a cylindrical shape, in accordance with one embodiment of the present invention.
Figure 10:
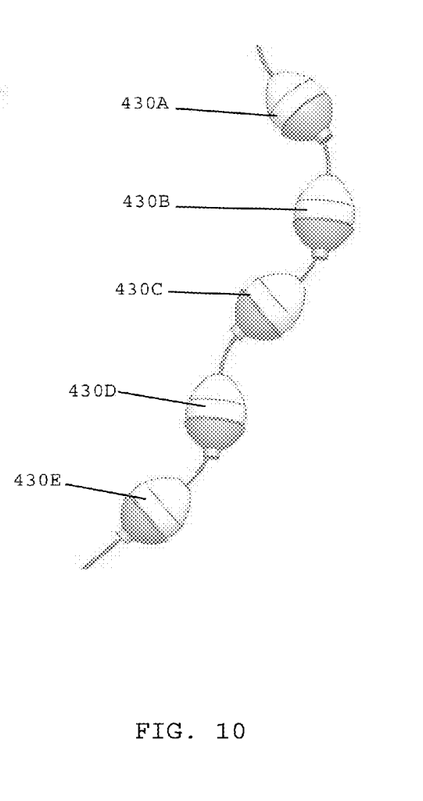
FIG. 10 shows a flexible absorbent and sealing system including a flexible cord and absorbent elements having an egg shape, in accordance with one embodiment of the present invention.

The absorbent elements may have a wide variety of geometric shapes. In the embodiment of FIG. 9, the absorbent elements 330A-330E have a cylindrical shape. In the embodiment of FIG. 10, the absorbent elements 430A-430E have an egg shape.

Figure 11:
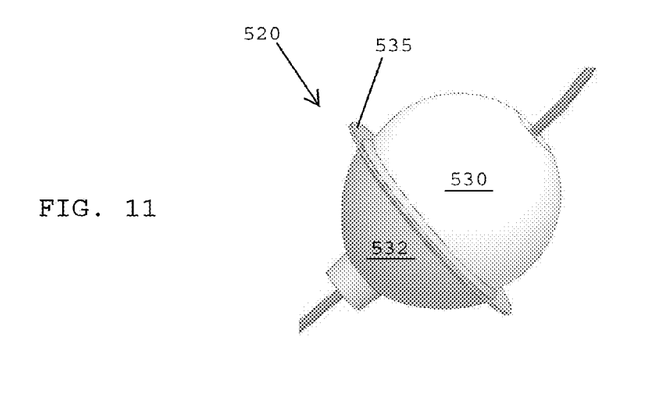
FIG. 11 shows an absorbent element and a distal end seal having a flexible protruding membrane, in accordance with one embodiment of the present invention.

Referring to FIG. 11, in one embodiment, a flexible absorbent and sealing system 520 preferably includes at least one absorbent element 530 having a distal end seal 532 having a relatively thin, flexible protruding membrane 535 located near the proximal rim of the sealing element 532. The protruding membrane 535 may be perpendicular to or may be angled in the proximal direction relative to the proximal end of a flexible cord. The protruding membrane 535 functions to further cup and/or collect dripping fluids as the absorbent elements are being removed from a trocar. The thin, flexible protruding membrane 535 may also serve to effectively communicate with a range of potentially larger trocar ports for enabling the removal of swollen absorbent elements with reduced fluid losses.

Figure 12:
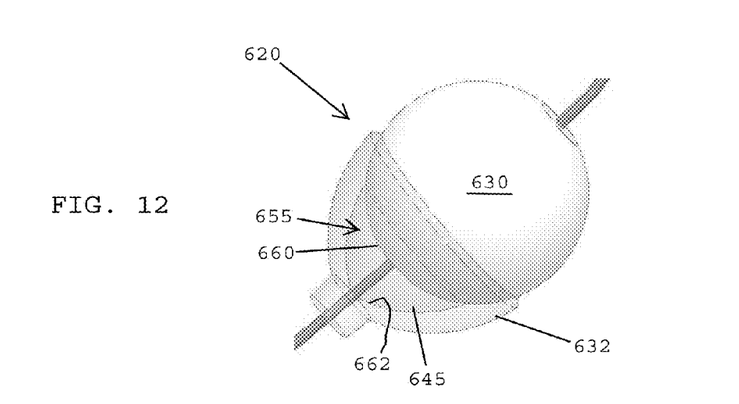
FIG. 12 shows an absorbent element and a distal end seal having an elongated reservoir, in accordance with another embodiment of the present invention.

Referring to FIG. 12, in one embodiment, a flexible absorbent and sealing system 620 preferably includes at least one absorbent element 630 and a distal end seal 632 covering a distal end of the absorbent element 630. In one preferred embodiment, a cup shaped proximal end of the distal end seal 632 preferably has an elongated reservoir 645 that is located distal to an absorbent element 630 thus creating a space 655 for the collection of fluids between the distal end 660 of the absorbent element 630 and the proximal face 662 of the elongated reservoir 645. In one embodiment, the volume of the reservoir may be adjusted in response to the degree of fluid management that is required or desired.

Figure 13:
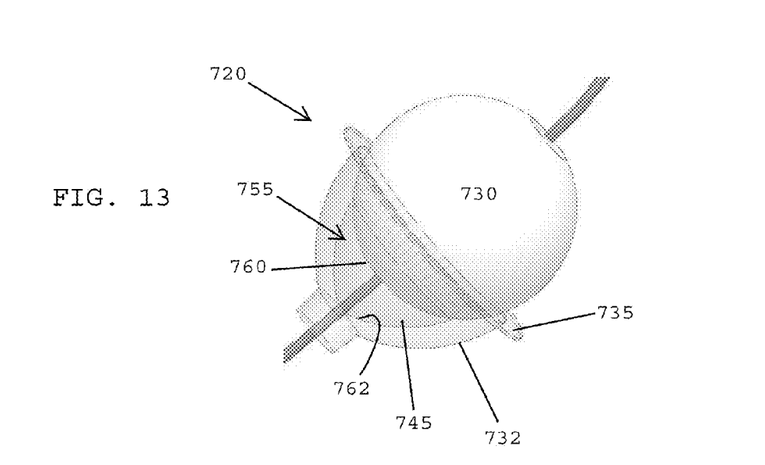
FIG. 13 shows an absorbent element and a distal end seal having a flexible protruding membrane and an elongated reservoir, in accordance with still another embodiment of the present invention.

Referring to FIG. 13, in one embodiment, a flexible absorbent and sealing system 720 preferably includes at least one absorbent element 730 and a distal end seal 732 that covers a distal end of the absorbent element 730. The distal end seal preferably has a relatively thin, flexible protruding membrane 735 located near the proximal rim of the sealing element 732 and an elongated reservoir 745 that is located distal to an absorbent element 730 thus creating a space 755 for the collection of fluids between the distal end 760 of the absorbent element 730 and the proximal face 762 of the elongated reservoir 745.

In one embodiment, a system may include a plurality of absorbent elements having distal end seals whereby one or more of the distal end seals has flexible protruding membranes and one or more of the distal end seals has elongated reservoirs.

Although one or more embodiments of the present application disclose using trocars, other embodiments of the present invention may utilize other devices having ports or elongated openings and still fall within the scope of the present invention.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for absorbing blood and bodily fluids during surgical procedures comprising:
    an elongated, flexible element having a proximal end and a distal end;
    a weight secured to the distal end of said elongated, flexible element;
    a plurality of absorbent elements attached to said elongated, flexible element, wherein said absorbent elements are adapted for soaking up blood and bodily fluids at a surgical site, and wherein said absorbent elements are spaced from one another along the length of said elongated, flexible element;
    a sealing element covering a distal end of a distal-most one of said plurality of absorbent elements, wherein said sealing element includes a flexible protruding membrane extending outwardly from a proximal rim located at a proximal end of said sealing element.

2. The system as claimed in claim 1, wherein said absorbent elements are selected from the group of absorbent elements consisting of sponges and cotton balls.

3. The system as claimed in claim 1, further comprising an anchor tab secured to the proximal end of said elongated, flexible element, wherein said absorbent elements are attached to said elongated, flexible element at positions that are closer to said weight than said anchor tab.

4. The system as claimed in claim 3, wherein said anchor tab comprises a pull ring secured to the proximal end of said elongated, flexible element.

5. The system as claimed in claim 3, wherein said anchor tab has a code provided thereon for auditing and accountability purposes.

6. The system as claimed in claim 1, wherein said sealing element comprises a grip element located at a distal end of said sealing element that is adapted to be held by a surgical tool for being moved about a surgical site for absorbing blood and bodily fluids.

7. The system as claimed in claim 6, wherein said sealing element has said proximal end having a cup shape that covers the distal end of said distal-most absorbent element, and wherein said grip element protrudes from the distal end of said cup shaped proximal end.

8. The system as claimed in claim 1, further comprising a sealing element covering a distal end of each of said absorbent elements, wherein at least one of said sealing elements includes an elongated reservoir that is located distal to one of said absorbent elements for defining a space for the collection of fluids between the distal end of the one of said absorbent elements and a proximal face of said elongated reservoir.

9. The system as claimed in claim 1, further comprising a surgical tool having an elongated, tubular opening with an inner diameter, wherein said sealing element has an outer diameter that matches or communicates with the inner diameter of said elongated, tubular opening.

10. The system as claimed in claim 9, wherein said surgical tool is a trocar and said elongated, tubular opening is a trocar opening.

11. A system for absorbing blood and bodily fluids during surgical procedures comprising:
    an elongated, flexible element having a proximal end and a distal end;
    a weight secured to the distal end of said elongated, flexible element;
    a plurality of absorbent elements attached to said elongated, flexible element, wherein said absorbent elements are spaced from one another along the length of said elongated, flexible element, and wherein said absorbent elements are adapted for soaking up blood and bodily fluids at a surgical site;
    a tab secured to the proximal end of said elongated, flexible element;
    a sealing element secured to and covering a distal end of at least one of said absorbent elements, wherein said sealing element includes a flexible protruding membrane extending outwardly from a proximal rim located at a proximal end of said sealing element.

12. The system as claimed in claim 11, further comprising:
    a trocar having a trocar opening with an inner diameter;
    wherein said sealing element has the proximal end having an outer diameter that matches the inner diameter of said trocar opening.

13. The system as claimed in claim 11, wherein said sealing element has a distal end including a gripping element that is adapted to be engaged by a surgical instrument for manipulating said absorbent element at a surgical site.

14. The system as claimed in claim 11, wherein said elongated, flexible element comprises a flexible core and said absorbent elements comprise sponges or cotton balls.

15. The system as claimed in claim 11, wherein said sealing element includes an elongated reservoir that is located distal to the at least one of said absorbent elements for defining a space for the collection of fluids between the distal end of the at least one of said absorbent elements and a proximal face of said elongated reservoir.

16. The system as claimed in claim 11, wherein said absorbent elements are closer to the distal end of said elongated, flexible element than the proximal end of said elongated, flexible element so that the proximal end of said elongated, flexible element remains outside of said trocar when said absorbent elements are positioned at the surgical site.

17. A system for absorbing blood and bodily fluids during surgical procedures comprising:
    an elongated, flexible element having a proximal end and a distal end;
    a weight secured to the distal end of said elongated, flexible element;
    a plurality of absorbent elements attached to said elongated, flexible element, wherein said absorbent elements are adapted for soaking up blood and bodily fluids at a surgical site, and wherein said absorbent elements are spaced from one another along the length of said elongated, flexible element;

a sealing element covering a distal end of a distal-most one of said plurality of absorbent elements, wherein said sealing element comprises a flexible protruding membrane extending outwardly from a proximal rim located at a proximal end of said sealing element and an elongated reservoir that is located distal to said distal-most absorbent element for defining a space for collecting fluids between the distal end of said distal-most absorbent element and a proximal face of said elongated reservoir.

18. The system as claimed in claim 17, wherein said proximal face of said elongated reservoir has a cup shape that covers the distal end of said distal-most absorbent element, and wherein said sealing element comprises a grip element located at a distal end of said sealing element that is adapted to be held by a surgical tool for moving said distal-most absorbent element about a surgical site for absorbing blood and bodily fluids.

* * * * *